United States Patent
Jangle et al.

(10) Patent No.: US 8,560,267 B2
(45) Date of Patent: Oct. 15, 2013

(54) IDENTIFYING ONE OR MORE ACTIVITIES OF AN ANIMATE OR INANIMATE OBJECT

(75) Inventors: Jeetendra Jangle, Fremont, CA (US); Vijay Nadkarni, San Jose, CA (US)

(73) Assignee: Imetrikus, Inc., Seattle, WA (US)

( * ) Notice: Subject to any disclaimer, the term of this patent is extended or adjusted under 35 U.S.C. 154(b) by 246 days.

(21) Appl. No.: 12/883,304

(22) Filed: Sep. 16, 2010

(65) Prior Publication Data

US 2011/0066383 A1    Mar. 17, 2011

Related U.S. Application Data

(63) Continuation-in-part of application No. 12/560,069, filed on Sep. 15, 2009, now abandoned.

(51) Int. Cl.
*G01C 22/00* (2006.01)

(52) U.S. Cl.
USPC ............. 702/160; 702/19; 702/141; 702/161

(58) Field of Classification Search
USPC ............. 702/19, 141, 160–161; 73/489–490, 73/492, 510, 865.4
See application file for complete search history.

(56) References Cited

U.S. PATENT DOCUMENTS

| | | | |
|---|---|---|---|
| 4,513,437 A | 4/1985 | Chainer et al. | |
| 6,028,626 A | 2/2000 | Aviv | |
| 6,265,982 B1 | 7/2001 | Ostwald | |
| 6,626,728 B2 | 9/2003 | Holt | |
| 6,675,649 B2 | 1/2004 | Uchiyama et al. | |
| 6,756,889 B2 | 6/2004 | Sala et al. | |
| 6,802,814 B2 | 10/2004 | Narimatsu | |
| 6,816,766 B2 | 11/2004 | Sala et al. | |
| 6,885,932 B2 | 4/2005 | Liu et al. | |
| 6,999,863 B2 | 2/2006 | Neal et al. | |
| 7,145,461 B2 | 12/2006 | Lehrman et al. | |
| 7,248,172 B2 | 7/2007 | Clifford et al. | |
| 7,301,526 B2 | 11/2007 | Marvit et al. | |
| 7,467,060 B2 | 12/2008 | Kulach et al. | |
| 7,715,982 B2 | 5/2010 | Grenfell et al. | |
| 7,827,000 B2 | 11/2010 | Stirling et al. | |
| 7,898,428 B2 * | 3/2011 | Dietz et al. | 340/670 |
| 8,060,337 B2 | 11/2011 | Kulach et al. | |
| 8,065,508 B2 * | 11/2011 | Rubin et al. | 713/1 |
| 2003/0158489 A1 | 8/2003 | Narimatsu | |
| 2005/0154512 A1 | 7/2005 | Schubert et al. | |
| 2006/0005578 A1 | 1/2006 | Tortoli | |
| 2006/0089538 A1 | 4/2006 | Cuddihy et al. | |
| 2006/0282021 A1 | 12/2006 | DeVaulet et al. | |

(Continued)

OTHER PUBLICATIONS

Fixler, 'Atom Interferometer-Based Gravity Gardiometer Measurements', 2003, pp. 1-138, Fixler Thesis.*

(Continued)

*Primary Examiner* — Sujoy Kundu
*Assistant Examiner* — Elias Desta
(74) *Attorney, Agent, or Firm* — Brian R. Short (57) ABSTRACT

Methods, systems and apparatus for identifying an activity of an animate or inanimate object are disclosed. One method includes identifying each elemental motion of a sequence of elemental motions of a device attached to the animate or inanimate object. The activity of the animate or inanimate object can be identified by matching the sequence of identified elemental motions of the device with a library of stored sequences of elemental motions, wherein each stored sequence of elemental motions corresponds with an activity.

27 Claims, 8 Drawing Sheets

(56) References Cited

U.S. PATENT DOCUMENTS

| | | |
|---|---|---|
| 2007/0167693 A1 | 7/2007 | Scholler et al. |
| 2007/0293781 A1 | 12/2007 | Sims et al. |
| 2008/0256796 A1 | 10/2008 | Fix |
| 2009/0303204 A1 | 12/2009 | Nasiri et al. |
| 2010/0073284 A1 | 3/2010 | Dods et al. |
| 2010/0121226 A1 | 5/2010 | Ten Kate et al. |
| 2010/0217533 A1 | 8/2010 | Nardkarni et al. |

OTHER PUBLICATIONS

International Application Published Under the Patent Cooperation Treaty (PCT), WO 2012/036958A3, Inventor: Jeetenda Jangle, PCT/US2011/050727.

\* cited by examiner

IDENTIFYING ONE OR MORE ACTIVITIES OF AN ANIMATE OR INANIMATE OBJECT

RELATED APPLICATIONS

This patent application is a continuation in part (CIP) of U.S. patent application Ser. No. 12/560,069 filed on Sep. 15, 2009, which is incorporated by reference.

FIELD OF THE DESCRIBED EMBODIMENTS

The described embodiments relate generally to monitoring motion. More particularly, the described embodiments relate to a method, system and apparatus for identifying one or more activities of an animate or inanimate object.

BACKGROUND

There is an increasing need for remote monitoring of individuals, animals and inanimate objects in their daily or natural habitats. Many seniors live independently and need to have their safety and wellness tracked. A large percentage of society is fitness conscious, and desire to have, for example, workouts and exercise regimen assessed. Public safety officers, such as police and firemen, encounter hazardous situations on a frequent basis, and need their movements, activities and location to be mapped out precisely.

The value in such knowledge is enormous. Physicians, for example, like to know their patients sleeping patterns so they can treat sleep disorders. A senior living independently wants peace of mind that if he has a fall it will be detected automatically and help summoned immediately. A fitness enthusiast wants to track her daily workout routine, capturing the various types of exercises, intensity, duration and caloric burn. A caregiver wants to know that her father is living an active, healthy lifestyle and taking his daily walks. The police would like to know instantly when someone has been involved in a car collision, and whether the victims are moving or not.

Existing products for the detection of animate and inanimate motions are simplistic in nature, and incapable of interpreting anything more than simple atomic movements, such as jolts, changes in orientation and the like. It is not possible to draw reliable conclusions about human behavior from these simplistic assessments.

It is desirable to have an apparatus and method that can accurately identify and monitor activities of an animate or inanimate object

SUMMARY

An embodiment includes a method of identifying an activity of an animate or inanimate object. The method includes identifying each elemental motion of a sequence of elemental motions of a device attached to the animate or inanimate object. The activity of the animate or inanimate object can be identified by matching the sequence of identified elemental motions of the device with a stored sequences of elemental motions, wherein each stored sequence of elemental motions corresponds with an activity.

Another embodiment includes an apparatus for identifying an activity of an animate or inanimate object. The apparatus includes a controller operative to identify each elemental motion of a sequence of elemental motions of device attached to the animate or inanimate object. The controller is further operative to identify the activity of the animate or inanimate object, comprising matching the sequence of identified elemental motions of the object with stored sequences of elemental motions, wherein each stored sequence of elemental motions corresponds with an activity.

Another embodiment includes a system for identifying an activity of a animate or inanimate object. The system includes means for identifying each elemental motion of a sequence of elemental motions of an device attached to the animate or inanimate object, and means for identifying the activity of the animate or inanimate object, comprising matching the sequence of identified elemental motions of the device with a library of stored sequences of elemental motions, wherein each stored sequence of elemental motions corresponds with an activity. The means for identifying each elemental motion includes means for generating an acceleration signature based on sensed acceleration of the device, means for matching the acceleration signature with at least one of a plurality of stored acceleration signatures, wherein each stored acceleration signatures corresponds with a type of motion, and means for identifying the type of motion of the device based on the matching of the acceleration signature with the stored acceleration signature.

Other aspects and advantages of the described embodiments will become apparent from the following detailed description, taken in conjunction with the accompanying drawings, illustrating by way of example the principles of the described embodiments.

DETAILED DESCRIPTION

The described embodiments include methods, systems and apparatuses that provide human activity and motion pattern recognition, allowing a determination of granular level activities of daily living being performed by a user. Embodiments of these granular feature determinations provide the capability to identify user safety. For example, a comprised safety situation, such as, the user falling down can be identified. By combining the granular motion actions and features with data from other sensors such as GPS (global positioning system), vital stats sensors and other inferred data such as time, it is possible to establish the high level activity being performed by the user. Knowledge of high level activities being performed during time periods such as a day allows for the building of various interesting applications that are useful for improving the quality of life of the users and their caregivers and to customize and optimize care plans. Armed with the knowledge of variation of peoples' behavior, repetitive and variant patterns across people, age, gender, location and time, systems can provide customized services for individuals and categories of people.

The monitoring of human activities generally falls into three categories: safety, daily lifestyle, and fitness. By carefully interpreting human movements it is possible to draw accurate and reasonably complete inferences about the state of well being of individuals. A high degree of sophistication is required in these interpretations. Simplistic assessments of human activity lead to inaccurate determinations, and ultimately are of questionable value. By contrast, a comprehensive assessment leads to an accurate interpretation and can prove to be indispensable in tracking the well being and safety of the individual.

To draw accurate inferences about the behavior of humans, it turns out that the atomic movements become simply alphabets that include elemental motions. Furthermore, specific sequences of elemental motions become the vocabulary that comprises human behavior. As an example, take the case of a person who leaves the home and drives to the shopping center. In such a scenario, the behavioral pattern of the person is walking to the door or the house, opening and closing the door, walking further to the car, settling down in the car, starting the engine, accelerating the car, going through a series of stops, starts and turns, parking the car, getting out and closing the car door, and finally walking to the shopping center. This sequence of human behavior is comprised of individual motions such as standing, walking, sitting, accelerating (in the car), decelerating, and turning left or right. Each individual motion, for example walking, is comprised of multiple atomic movements such as acceleration in an upward direction, acceleration in a downward direction, a modest forward acceleration with each step, a modest deceleration with each step, and so on.

With written prose, letters by themselves convey almost no meaning at all. Words taken independently convey individual meaning, but do not provide the context to comprehend the situation. It takes a complete sentence to obtain that context. Along the same line of reasoning, it requires a comprehension of a complete sequence of movements to be able to interpret human behavior.

Although there is an undeniable use for products that are able to detect complex human movements accurately, the key to the success of such technologies lies in whether users adopt them or not. The technology needs to capture a wide range of human activities. The range of movements should ideally extend to all types of daily living activities that a human being expects to encounter—sleeping, standing, walking, running, aerobics, fitness workouts, climbing stairs, vehicular movements, falling, jumping and colliding, to name some of the more common ones.

It is important to detect human activities with a great deal of precision. In particular, activities that relate to safety, fitness, vehicular movements, and day to day lifestyle patterns such as walking, sleeping, climbing stairs, are important to identify precisely. For example, it is not enough to know that a person is walking. One needs to know the pace and duration of the walk, and additional knowledge of gait, unsteadiness, limping, cadence and the like are important.

It is critical that false positives as well as false negatives be eliminated. This is especially important for cases of safety, such as falls, collisions, and the like. Human beings come in all types—short, tall, skinny, obese, male, female, athletic, couch potato, people walking with stick/rolator, people with disabilities, old and young. The product needs to be able to adapt to their individuality and lifestyle.

The embodiments described provide identification of types of motion of an animate or inanimate object. Motion is identified by generating acceleration signatures based on the sensed acceleration of the object. The acceleration signatures are compared with a library of motion signature, allowing the motion of the object to be identified. Further, sequences of the motions can be determined, allowing identification of activities of, for example, a person the object is attached to.

Just as the handwritten signatures of a given human being are substantively similar from one signature instance to the next, yet have minor deviations with each new instance, so too will the motion signatures of a given human be substantively similar from one motion instance to the next, yet have minor deviations.

Algorithms used for pattern recognition (signature matching) should have the sophistication to accurately handle a wide range of motions. Such algorithms should have the ability to recognize the identical characteristics of a particular motion by a given human being, yet allow for minor variations arising from human randomness. Additionally, the devices used to monitor peoples' movement need to be miniature and easy to wear. These two objectives are fundamentally opposed. However, the described embodiments provide a single cohesive device and system that is both sophisticated enough to detect a wide range of motions.

Figure 1:
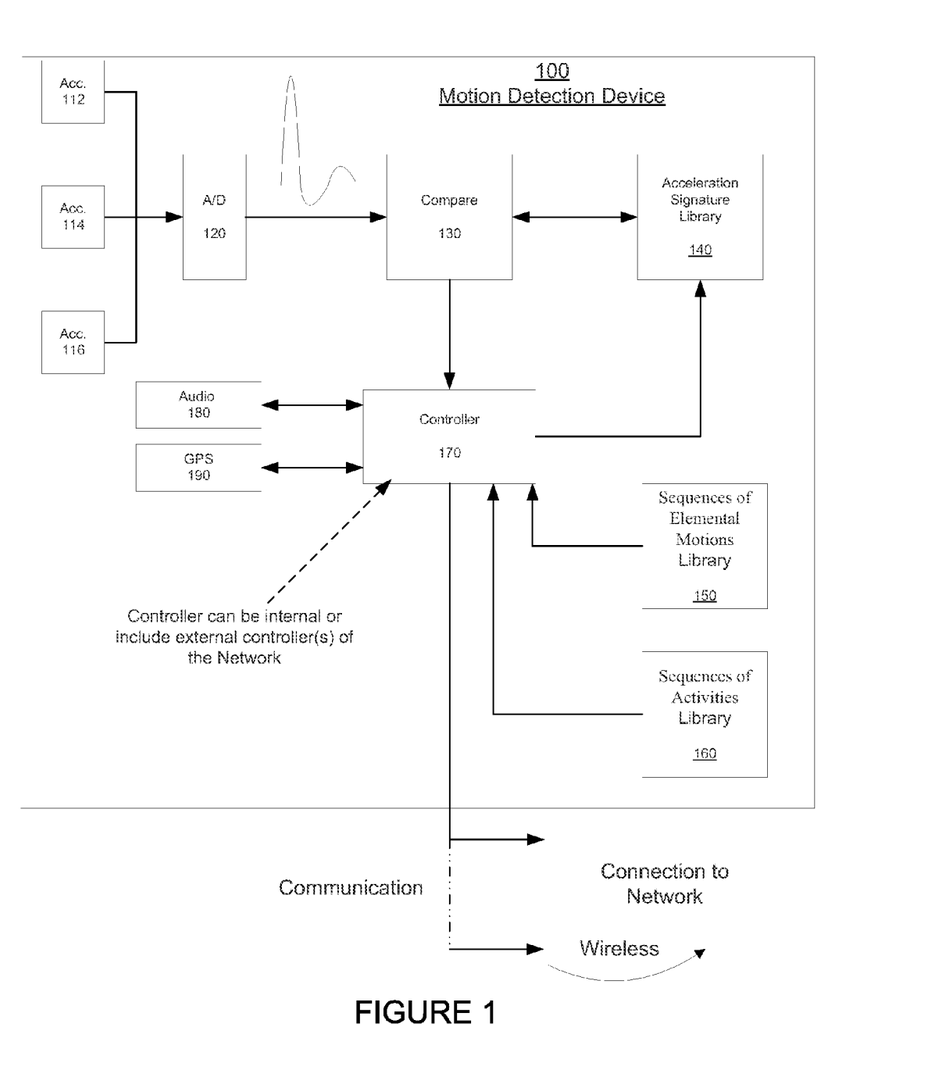
FIG. 1 shows an example of a block diagram of a motion-detection and tracking device.

FIG. 1 shows an example of a block diagram of a motion-detection and tracking device. The motion detection device can be attached to an animate or inanimate object, and therefore, motion of the object that can be detected and identified. Based on the identified motion, estimates of the behavior and conditions of the object can be determined.

The motion detection device includes sensors (such as, accelerometers) that detect motion of the object. One embodiment of the sensors includes accelerometers 112, 114, 116 that can sense, for example, acceleration of the object in X, Y and Z directional orientations. It is to be understood that other types of motion detection sensors can alternatively be used.

An analog to digital converter (ADC) digitizes analog accelerometer signals. The digitized signals are received by compare processing circuitry 130 that compares the digitized accelerometer signals with signatures that have been stored within a library of signatures 140. Each signature corresponds with a type of motion. Therefore, when a match between the digitized accelerometer signals and a signature stored in the library 140, the type of motion experienced by the motion detection device can determined.

An embodiment includes filtering the accelerometer signals before attempting to match the signatures. Additionally, the matching process can be made simpler by reducing the possible signature matches.

An embodiment includes identifying a previous human activity, context. That is, for example, by knowing that the previous human activity was walking, certain signatures can intelligently be eliminated from the possible matches of the present activity that occurs subsequent to the previous human activity (walking).

An embodiment includes additionally reducing the number of possible signature matches by performing a time-domain analysis on the accelerometer signal. The time-domain analysis can be used to identify a transient or steady-state signature of the accelerometer signal. That is, for example, a walk may have a prominent steady-state signature, whereas a fall may have a prominent transient signature. Identification of the transient or steady-state signature of the accelerometer signal can further reduce or eliminate the number of possible signature matches, and therefore, make the task of matching the accelerometer signature with a signature within the library of signature simpler, and easier to accomplish. More specifically, the required signal processing is simpler, easier, and requires less computing power.

A controller 170 manages the signature matching and identification. As will be described, the controller 170 can be connected to an external network. The processing of the controller 170 can be performed locally or distributed amongst other controller through the network. Determination of where processing takes place (that is, what controller or processor) can be based on a balance of speed of the processing, and power of the local controller (that is, power required of a controller within a mobile device). The controller 170 also manages the activity identification based on sequences of motion, and manages the identifications of behaviors based on the identified activities as will be described. A sequences of elemental motions library 150 can be used for matching the sequences of motion to a particular activity. A sequences of activities library 160 can be used for matching sequences of activities to a particular behavior. Again, the processing of the controller 170, as well as the libraries 150, 160, 170 can be distributed across the network through a wired or wireless connection.

Upon detection of certain types of motion, an audio device 180 and/or a global positioning system (GPS) 190 can engaged to provide additional information that can be used to determine the situation of, for example, a human being the motion detection device is attached to.

The condition, or information relating to the motion detection device can be communicated through a wired or wireless connection. A receiver of the information can process it, and make a determination regarding the status of the human being the motion detection device is attached to. Information and history of a user of the motion detection device can be utilized to characterize the user/

Figure 2:
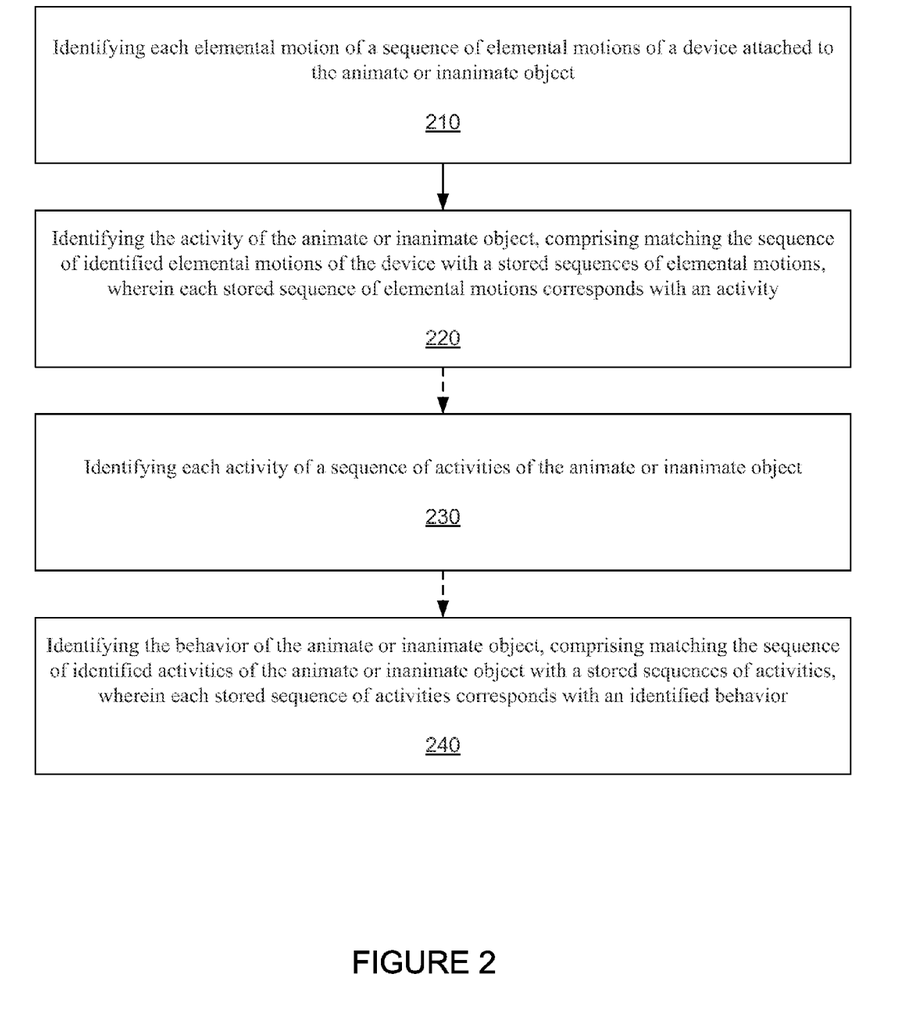
FIG. 2 is a flow chart that includes steps of an example of a method of identifying an activity of a animate or inanimate object.

FIG. 2 is a flow chart that includes steps of an example of a method of identifying an activity of an animate or inanimate object. A first step 210 includes identifying each elemental motion of a sequence of elemental motions of a device attached to the animate or inanimate object. A second step 220 includes identifying the activity of the animate or inanimate object, comprising matching the sequence of identified elemental motions of the device with stored sequences of elemental motions, wherein each stored sequence of elemental motions corresponds with an activity.

A plurality or sequence of identified activities of, for example, a human being, can be used to identify a behavior of the human being. As such, a third step 230 includes identifying each activity of a sequence of activities of the animate or inanimate object. A fourth step 240 includes identifying the behavior of the animate or inanimate object, comprising matching the sequence of identified activities of the animate or inanimate object with a stored sequences of activities, wherein each stored sequence of activities corresponds with an identified behavior.

The animate or inanimate object can be many things, such as, a human being or an animal. Alternatively or additionally, the animate or inanimate object can be an object associated with a human being, such as, a vehicle. The device can be attached to the animate or inanimate object in many different ways. For example, the device can be attached to a human being, or clothing (pants, shirt, jacket, and/or hat) being worn by the human being. The device can be within a pendant or necklace being worn by the human being. The device can be attached, for example, to a vehicle being operated by the human being.

For an embodiment, identifying each elemental motion includes generating an acceleration signature based on sensed acceleration of the device, matching the acceleration signature with at least one of a plurality of stored acceleration signatures, wherein each stored acceleration signatures corresponds with a type of motion, and identifying the type of motion of the device based on the matching of the acceleration signature with the stored acceleration signature.

Other factors can be used to refine (improve) the identification of the activity. These factors can include, for example, analyzing timing of the identified activity. For an embodiment, the timing includes at least one of an hour of a day, a day of a week, a week of a month, a month of a year. Other factors include analyzing at least one identified location of the identified activity, analyzing a rate of change of a location of the animate or inanimate object, analyzing patterns of a plurality of identified activities, and/or analyzing an age of the animate or inanimate object.

As previously mentioned, behaviors can be identified based on sequences of identified activities. Embodiments further include tracking at least one behavior of the animate or inanimate object over time. One embodiment includes identifying patterns of the at least one behavior. An embodiment includes grouping the patterns of the animate or inanimate objects based on a common parameter between the animate or inanimate objects. Embodiments include identifying changes in at least one behavior of the animate or inanimate object. An embodiment further includes sending an alert upon identification of predetermined set of behavior changes.

Figure 3:
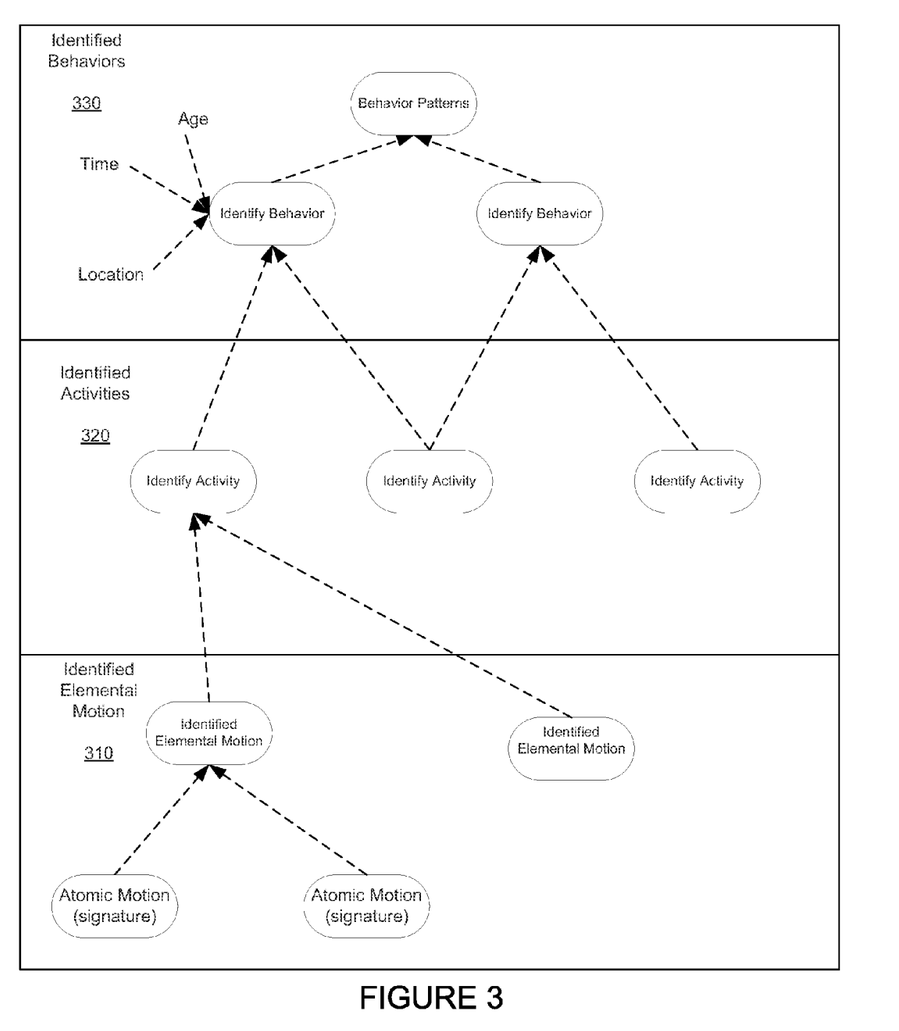
FIG. 3 shows an example of hierarchical relationships between elemental motions, activities, behaviors and behavioral patterns.

FIG. 3 shows an example of hierarchical relationships between elemental motions, activities, behaviors and behavioral patterns. At the lowest level of the hierarchy are the identified elemental motions 310. As described, the elemental motions can be identified by sensing signatures of motion (by, for example, accelerometers within a device attached to a user) and matching the signatures within known signatures. At the next higher level of the hierarchy are the identified activities 320. As described, the activities can be identified by matching determined sequences of elemental motions with previously known sequences of elemental motions. At the next higher level of the hierarchy are identified behaviors 330. As described, the behaviors can be identified by matching determined sequences of activities with previously known sequences of activities. Each of the levels of hierarchy can be aided with additional information. For example, the identified behaviors can be more intelligently identified with time, location and or age of the user. Additionally, this information can be used for grouping and identified behavior patterns. Once a behavior pattern has been associated with a user, much more useful information can be associated with the user.

The described embodiments can correlate the sequences of activity data being generated along with the ambient information like location, time, etc to generate daily patterns of the user. These daily patterns then emerge as behavioral patterns of the person. Behavioral patterns allow the system to determine how people spend their time, recreational and buying habits, interests of people, and pattern variations across demographics etc. Based on the behavioral patterns, how habits of people vary in relationship to time and their physical wellbeing can be deduced or inferred.

The described embodiment includes systems that can detect critical conditions based on the previous knowledge obtained by the systems for an individual and help prevent and aid safety situations. Additionally, the systems can detect early signs of conditions that enable early attention from experts. Additionally, the systems can learn from observation and capture behavior patterns that cannot be determined with generic real-time monitoring. The systems adapt to the observed person using the data being collected through monitoring.

Descriptively, an analogy can be drawn between a person's motions and languages. For example person has minute motions, activities, daily lifestyle, behavioral patterns and analogous to word, sentences, paragraph, chapters and books. As there are words in the vocabulary, vocabulary can be created of elemental motions. The way sentences are created with putting words into certain order, the elemental motions can be put into certain order and form activities. Activities can be put in succession along with ambient parameters and form contextual activities. Series of contextual activities or data mining of activities per day/week can form a lifestyle of a person, which can lead to behavioral patterns of a person.

Analogies include, for example, Sound→Atomic motion, Alphabets→Elemental Motion, Orientation, Words→Basic Movements, Sentences→Compound Movements, Paragraph→Contextual Movements, Chapters→Activity Pattern, Books→Behavioral Patterns.

A person's lifestyle or behavior can be determined based on his/her movement patterns. Small movement (elemental motion) patterns can be determined by the 3 dimensional acceleration signals and orientation. Examples of elemental motions include, for example, arm movement, sitting sedentary in the chair, getting up from the chair, standing, walking, running, falling. Putting the movement patterns basic components in series (varied combinations) provides a high degree of inference of the activity. Inference can made using the metrics of elemental motions and metrics of ambient variables. Examples of ambient variables include time of the day, GPS location, environment, and/or physical nature.

The following is an example of a series (sequence) of higher-level contextual activities includes that each includes a sequence of elemental motions. A first example of a higher level activity includes a user going to a grocery store. First, the user leaves his/her house which can include the following elemental motions/activities. Leaving the house can be detected as including the following sequence of elemental motions: getting up from chair, walking few steps, stopping briefly at the door, and walking to the car. Next, can include: identifying the user driving a car, including the following sequence of elemental motions: sitting into the car, driving the car, car movements, parking of car, getting out of car, with the additional inputs of, for example, location and time of the day. The next step can include identifying that the user walked to the grocery store at the location.

Other identified activities can include identifying the user getting up in the morning, by identifying the following sequence of elemental motions and inputs: identifying the time of the day (night), identifying sleeping, or long sedentary activity, identifying going to the bathroom and rolling over in the sleep. The activity of sitting in a car can include identifying the following sequence of elemental motions: opening the door, sitting down in the car, closing the door, pulling on the belt, putting on the seat belt, and sitting back in the seat. The activity of driving can be identified by identifying the following sequence of elemental motions (influence, for example, by location and time of the day): sitting in the car, starting the car, the car moving, stopping the car, opening the car door, getting out of the car, closing the car door. Identification of car movement can include identifying the following sequence of elemental motions: going forward, going backward, driving, braking, turning left, and turning right.

Higher-level activity identification can include, for example, monitoring a duration of sleep including identifying a number of times woke up and leaving the bed, duration away from bed, duration of deep sleep and number of deep sleeps at night, start and end time of sleep. This information can be used to establish long term trends of sleep including determining when the person (user) goes to bed, how long it takes to fall asleep, quality of sleep, and/or length of sleep. If there is a sudden departure from the established sleep pattern, for example, frequent visits to the bathroom at night, this could indicate signs of distress or unease requiring a visit from caregivers or visit to physician. Additional sensors like temperature and/or blood pressure could be triggered automatically to take vital stats at certain intervals and transmitted to a physician for study prior to visit in such scenarios. Such a system can also predict the change in sleep cycles and when the person should move in his/her sleep. If this does not happen, the system could again trigger the vital stats sensors and breathing motion sensor to determine if the person is alright (alive), and sound emergency if needed.

The system can also be useful for identifying safety patterns. For example, if a person has recurring falls, behavior patterns can be used for fall prevention. Falls and the sequences of information leading up to a fall can be monitored. Therefore, predictions can be made about the behavior that typically occurs before a fall. By mining the collected behavior data it is possible to infer and help the person to reduce/prevent further falls. As such, various applications can include, for example, fall prevention, identifying changes in behavior indicating pain and/or sickness, identifying that a person is lost and moving in circles, randomly, or wandering, identifying that a person is acting aggressively.

Other safety patterns include behavior while driving. Based on how the person drives car, one can determine whether the person being monitored is a safe driver or unsafe driver. Unsafe driving behavior can be identified based on, for example, jerky, erratic motions, and/or excessive speed, collisions and jackrabbit acceleration. Another way to deduce unsafe driving behavior is by the type of movements of a person while driving the vehicle. Safe driving behavior can be identified by driving speed, the way the turns are taken, stops, etc. The safe and unsafe driving behavior can be monitored and used for many different purposes.

At least some of the described embodiment include a system that can be used to determine and analyze the lifestyle the person is leading based on the past motion activity data. The system can then suggest changes to life patterns and daily activities to towards improvements towards a healthier and safe lifestyle. The system adapts to the changing lifestyle of the person and can continuously monitor the progress. Caregivers and physicians can provide the suggested activities to help the person live a better lifestyle. The system in the process of monitoring can detect the variance from the suggested activity level and let self, caregivers or physicians manage the change.

Figure 4A:
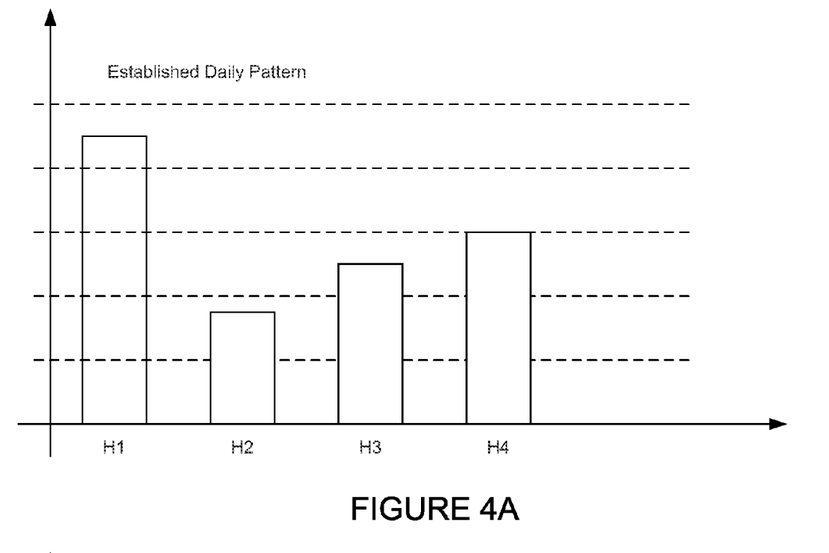
FIGS. 4A, 4B are plots that show examples of an established activity pattern and a daily activity pattern for an animate or inanimate object, allowing for detection of changes in behavior.
Figure 4B:
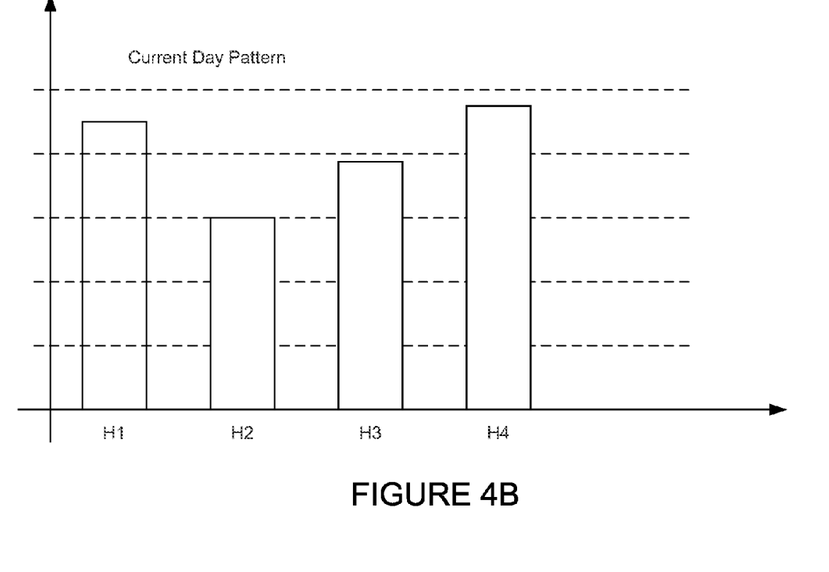

FIGS. 4A, 4B are plots that show examples of an established activity pattern and a daily activity pattern for an animate or inanimate object, allowing for detection of changes in behavior. The plot of FIG. 4A shows the accumulated results of monitoring the behavior of a user. The results can be plotted, for example, to depict for each hour, for example, after the user wakes up in the morning. This plot can adaptively change over time. The plot of FIG. 4B shows an exemplary plot that could be generated for a currently monitored day. The deviation in the activity pattern of the user can provide an indicator of a condition of the user. Some identified conditions, such as, sluggish behavior can trigger an alert.

Figure 5A:
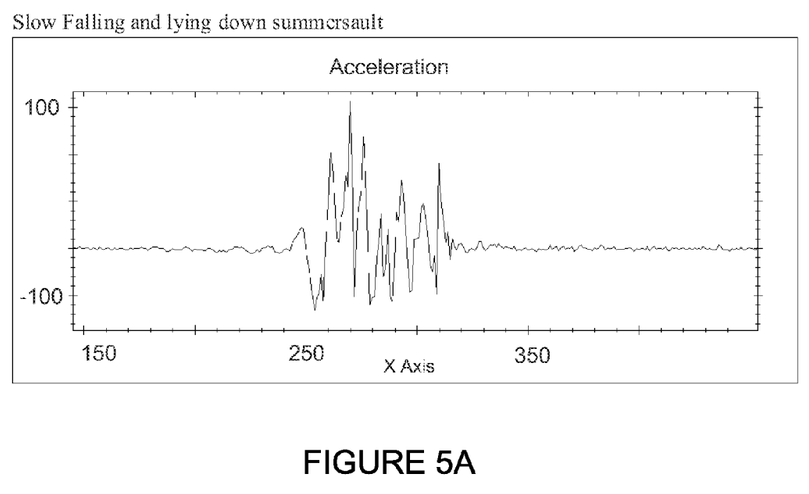
FIGS. 5A, 5B shows examples of time-lines of several different acceleration curves (signatures), wherein each signature is associated with a different type of sensed or detected motion.
Figure 5B:
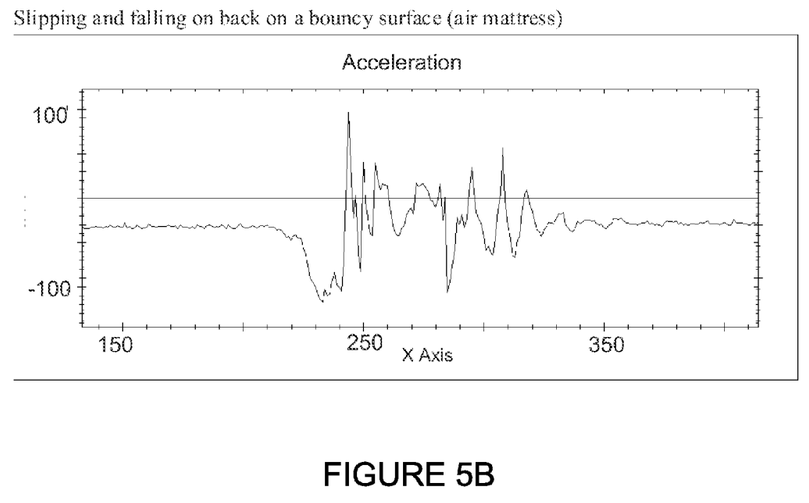

FIGS. 5A, 5B shows examples of different types of acceleration and orientation signatures for various sample motions by human beings. It should be noted that these signatures are expected to have certain components that are common from one human being to the next, but also have certain components that vary from one human to the next.

The signatures of FIGS. 5A, 5B are depicted in only one orientation. That is, three accelerometers can be used to generate acceleration signatures in the X, Y and Z (three) orientations. The signatures of FIGS. 5A, 5B only show the signature of one of the three orientations. It is to be understood that matching can use the other orientations as well.

FIG. 5A shows an example of an acceleration signature of a person doing a slow fall and lying down summersault. FIG. 5B shows an example of an acceleration signature of a person slipping and falling back on a bouncy surface (for example, an air mattress). By matching an acceleration signature that has been generated by sensing the motion of a person with one of many stored signatures, the motion of the person can be determined.

Figure 6:
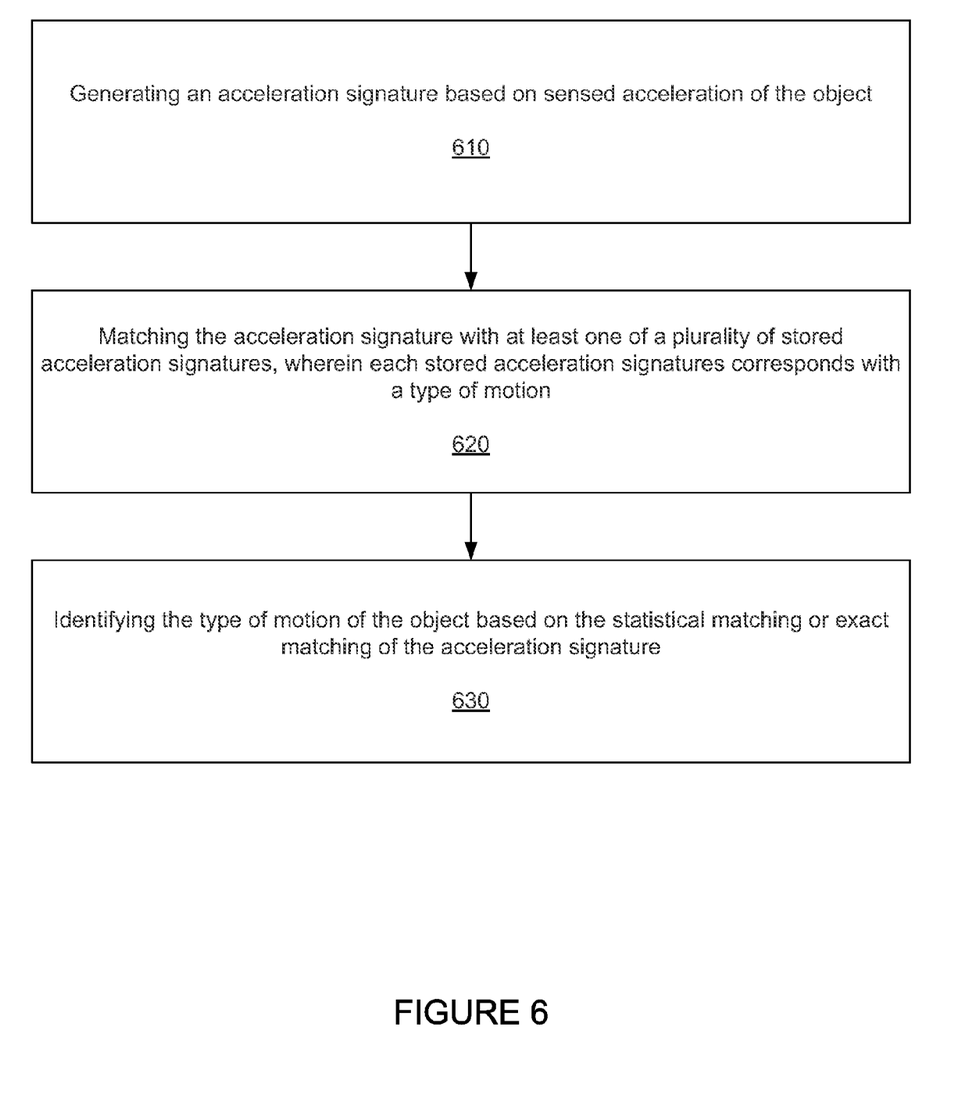
FIG. 6 is a flow chart that includes the steps of one example of a method of identifying a type of motion of an animate or inanimate object.

FIG. 6 is a flow chart that includes the steps of one example of a method of identifying a type of motion of an animate or inanimate object. A first step 610 includes generating an acceleration signature (for example, a tri-axial) based on the sensed acceleration of the object. A second step 620 includes matching the acceleration signature with at least one of a plurality of stored acceleration signatures, wherein each stored acceleration signatures corresponds with type of motion. A third step 630 includes identifying the type of motion of the object based on the statistical (pattern) matching or exact matching of the acceleration signature. The acceleration signal can be created using a wavelet transformation.

For embodiments, the type of motion includes at least one of atomic motion, elemental motion and macro-motion.

Though embodiments of generating matching acceleration signatures are described, it is to be understood that additional or alternate embodiments can include generating and matching of orientation and/or audio signatures. Correspondingly, the first step 610 can include generating an acceleration signature, (and/or) orientation and audio signature based on the sensed acceleration, orientation of the object and audio generated by the object, for example, a thud of a fall, or a cry for help.

Atomic motion includes but is not limited to a sharp jolt, a gentle acceleration, complete stillness, a light acceleration that becomes stronger, a strong acceleration that fades, a sinusoidal or quasi-sinusoidal acceleration pattern, vehicular acceleration, vehicular deceleration, vehicular left and right turns, and more.

Elemental motion includes but is not limited to motion patterns for walking, running, fitness motions (e.g. elliptical machine exercises, rowing, stair climbing, aerobics, skipping rope, bicycling . . . ), vehicular traversal, sleeping, sitting, crawling, turning over in bed, getting out of bed, getting up from chair, and more.

Macro-motion includes but is not limited to going for a walk in the park, leaving home and driving to the shopping center, getting out of bed and visiting the bathroom, performing household chores, playing a game of tennis, and more.

Each of the plurality of stored acceleration signatures corresponds with a particular type of motion. By matching the detected acceleration signature of the object with at least one of a plurality of stored acceleration signatures, an estimate or educated guess can be made about the detected acceleration signature.

An embodiment includes a common library and a specific library, and matching the acceleration signature includes matching the acceleration signature with stored acceleration signatures of the common library, and then matching the acceleration signature with stored acceleration signatures of the specific library. For a particular embodiment, the general library includes universal acceleration signatures, and the specific library includes personal acceleration signatures. That is, for example, the stored acceleration signatures of the common library are useable for matching acceleration signatures of motions of multiple humans, and the stored acceleration signatures of the specific library are useable for matching acceleration signatures of motions of a particular human. Additionally, each library can be further categorized to reduce the number of possible matches. For example, at an initialization, a user may enter physical characteristics of the user, such as, age, sex and/or physical characteristics (such as, the user has a limp). Thereby, the possible signatures matches within the general library can be reduced. The signature entries within the specific library can be learned (built) over time as the human wearing the motion detection device goes through normal activities of the specific human. The specific library can be added to, and improved over time.

An embodiment includes filtering the acceleration signals. Additional embodiment include reducing the number of stored acceleration signature matches by identifying a previous activity of the object, and performing a time domain analysis on the filtered acceleration signal to identify transient signatures or steady-state signatures of the filtered acceleration signal. That is, by identifying a previous activity (for example, a human walking of sleeping) the possible number of present activities can be reduced, and therefore, the number of possible stored acceleration signature matches reduced. Additionally, the transient and/or steady-state signatures can be used to reduce the number of possible stored acceleration signature matches, which can improve the processing speed.

Another embodiment includes activating audio sensing of the object if matches are made with at least portions of particular stored acceleration signatures. For example, if the acceleration signature exceeds a threshold value, then audio sensing of the object is activated. This is useful because the audio information can provide additional clues as to what, for example, the condition of a person. That is, a fall may be detected, and audio information can be used to confirm that a fall has in fact occurred.

Another embodiment includes transmitting the sensed audio. For example, of a user wearing the object has fallen, and the fall has been detected, audio information can be very useful for determining the condition of the user. The audio information can allow a receiver of the audio information to determine, for example, if the user is in pain, unconscious or in a dangerous situation (for example, in a shower or in a fire).

An embodiment includes the object being associated a person, and the stored acceleration signatures corresponding with different types of motion related to the person. A particular embodiment includes identifying an activity of the person based on a sequence of identified motions of the person. The activity of the person can include, for example, falling (the most important in some applications), walking, running, driving and more. Furthermore, the activities can be classified as daily living activities such as walking, running, sitting, sleeping, driving, climbing stairs, and more, or sporadic activities, such as falling, having a car collision, having a seizure and so on.

An embodiment includes transmitting information related to the identified type of motion if matches are made with particular stored acceleration signatures. The information related to the identified type of motion can include at least one of motions associated with a person the object is associated with. The motions can include, for example, a heartbeat of the person, muscular spasms, facial twitches, involuntary reflex movements which can be sensed by, for example, an accelerometer. Additionally, the information related to the identified type of motion can include at least one of location of the object, audio sensed by the object, temperature of the object.

Another embodiment includes storing at least one of the plurality of stored acceleration signatures during an initialization cycle. The initializing cycle can be influenced based on what the object is attached to. That is, initializing the stored acceleration signatures (motion patterns) can be based on what the object is attached to, which can both reduce the number of signatures required to be stored within, for example, the general library, and reduce the number of possible matches and reduce the processing required to identify a match. Alternatively or additionally, initializing the stored acceleration signatures can be based on who the object is attached to, which can influence the specific library. The initialization can be used to determine motions unique, for example, to an individual. For example, a unique motion can be identified for a person who walks with a limp, and the device can be initialized with motion patterns of the person walking with a limp.

An embodiment includes initiating a low-power sleep mode of the object if sensed acceleration is below a threshold for a predetermined amount of time. That is, if, for example, a person is sensed to be sleeping, power can be saved by de-activating at least a portion of the motion sensing device.

Various methods can be used for sequence and/or signature matching. For example, one embodiment includes formation of macro motion signatures. The macro motion signatures are built from an output of state analysis vectors using known wavelet transformation techniques (for example, a Haar Transform). The transform performs pattern matching on current motion pattern with existing motion pattern library using, for example, DWT (Discreet Wavelet Transform) techniques. Complex motion wavelets are later matched using statistical pattern matching techniques, such as, HHMM (Hidden Heuristic Markov Model). The statistical pattern matching includes detecting and classifying events of interest. The events of interest are built by observing various motions and orientation states data of an animate or inanimate object. This data is used to train the statistical model which performs the motion/activity detection. Each activity has its own model trained based on the observed data. Embodiments can further include a learning system providing the right model for the user from a set of model. The learning system can aid in building newer (personal) patterns which are not in the library for the person who is wearing the motion detection device. Embodiments further include pre-building a motion database of motion libraries against which motion signatures are compared. The database adds new motion/states signature dynamically as they are identified.

Figure 7:
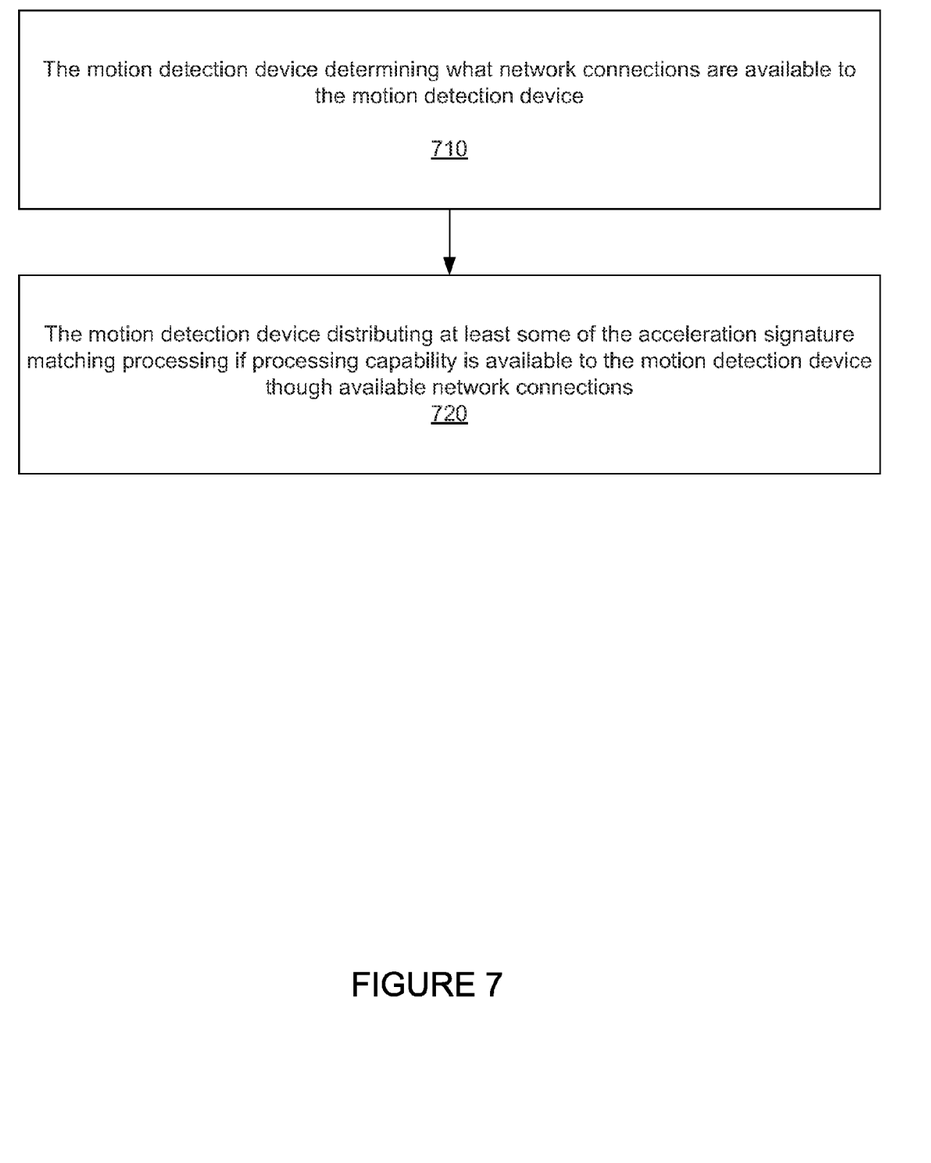
FIG. 7 is a flow chart that includes steps of one example of a method of a motion detection device checking network availability for improvements in speed and/or processing power of acceleration signature matching.

FIG. 7 is a flow chart that includes steps of one example of a method of a motion detection device checking network availability for improvements in speed and/or processing power of acceleration signature matching, wherein the motion detection device includes motion detection sensors that generate the acceleration signal. A first step 710 includes the motion detection device determining what network connections are available to the motion detection device. A second step 710 includes the motion detection device distributing at least some of the acceleration signature matching processing if processing capability is available to the motion detection device though available network connections.

For an embodiment, the motion detection device distributes the acceleration signature matching processing if the processing capability is available to the motion detection device though available network connections, and distributing the acceleration signature matching processing saves the motion detection device processing power. Another embodiment, the motion detection device distributes the acceleration signature matching processing if the processing capability is available to the motion detection device though available network connections, and distributing the acceleration signature matching processing increases a speed of the motion detection device processing. Alternatively, the motion detection device distributes the processing to optimize both power and processing speed. Additionally, the processing distribution can be dependent upon the bandwidths of the available network connections. That is, some networks connections can generally support higher data transfer rates, and therefore, influence the processing speed.

Generally, the motion detection device scales its processing to the level of processing available. That is, as additional processing power becomes available to the motion detection device, the motion detection device can increase the complexity of the signature matching processing. The processing can be distributed as processing capability becomes available through network connections. The processing can be performed in different locations as network connectivity becomes available, which can advantageously reduce the power consumption of the motion detection device and/or increase the speed of the processing.

Figure 8:
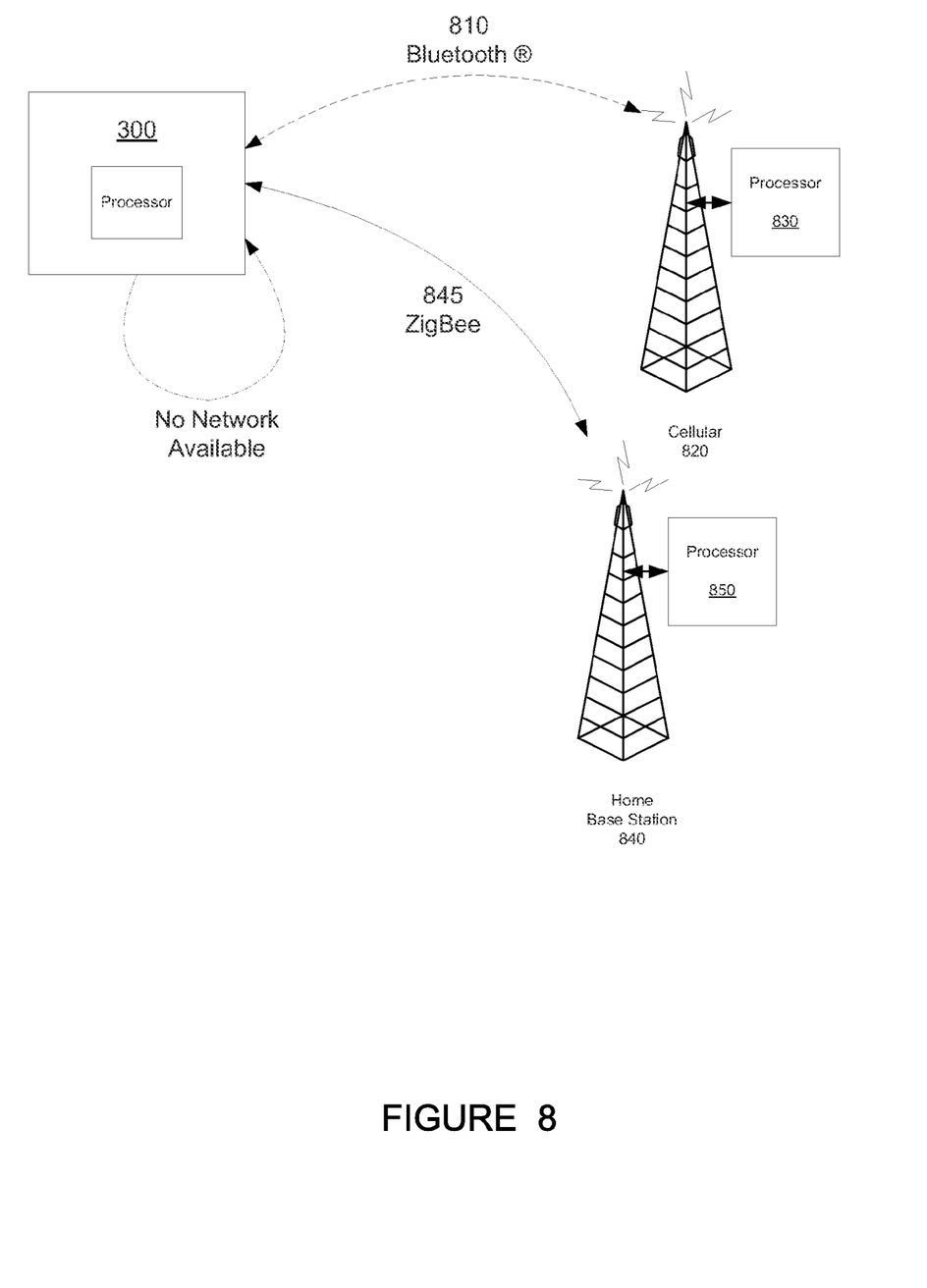
FIG. 8 shows an example of a motion detection and tracking device that can be connected to one of multiple networks.

FIG. 8 shows a motion detection device 300 that can be connected to one of multiple networks. Examples of possible networks (not a comprehensive list) the motion detection device 300 can connect to, include a cellular network 820 through, for example, a Bluetooth® wireless link 810, or to a home base station 840 through, for example, a Zigbee wireless link 845. The wireless links 810, 845 can each provide different levels of bandwidth. Each of the networks includes available processing capabilities 830, 850.

If the motion detection device 300 does not have any network connections available, the motion detection device 300 must perform its own matching processing. If this is the case, then the processing algorithms may be less complex to reduce processing power, and/or reduce processing speed. For example, the matching processing can be made simpler by comparing threshold levels for elemental motions by extracting significant wavelet coefficients. Acceleration signals data acquisition is performed in chunk of processing every few mili-seconds by waking up. For all other times the processor rests in low-power mode. Except for the emergency situation, the RF communication is done periodically when the data is in steady state, there is no need to send it to network i.e. when the object is in sedentary there is no need to send data change in the state is communicated to network. Additionally, if no network connections are available, the operation of the motion detection device 300 may be altered. For example, if the motion detection device 300 detects an emergency situation (such as, a fall), the motion detection device 300 may generate an audio alert. If a network connection was available, the audio alert may not be generated, but an alert may be transmitted over the available network.

The motion detection device 300 includes a controller in which at least a portion of the analysis and signature matching can be completed. However, if the motion detection device 300 has one or more networks available to the motion detection device 300, the motion detection device can off-load some of the processing to one of the processors 830, 850 associated with the networks. The processing required for identification of motion, activity; behavior, and/or behavior patterns can all be distributed across the network as selected.

The determination of whether to off-load the processing can be based on both the processing capabilities provided by available networks, and the data rates (bandwidth) provided by each of the available networks.

Although specific embodiments have been described and illustrated, the embodiments are not to be limited to the specific forms or arrangements of parts so described and illustrated.

What is claimed:

1. A method of identifying an activity of an animate or inanimate object, comprising:
    identifying, by one or more processors, each elemental motion of a sequence of elemental motions of a device attached to the animate or inanimate object; and
    identifying, by the one or more processors, the activity of the animate or inanimate object, comprising matching the sequence of identified elemental motions of the device with a library of stored sequences of elemental motions, wherein each stored sequence of elemental motions corresponds with an activity;
    wherein identifying each elemental motion comprises:
    generating an acceleration signature based on sensed acceleration of the device;
    matching, by the one or more processors, the acceleration signature with at least one of a plurality of stored acceleration signatures, wherein each stored acceleration signatures corresponds with a type of motion;
    identifying, by the one or more processors, the type of motion of the device based on the matching of the acceleration signature with the stored acceleration signature;
    wherein the type of motion comprises at least one of atomic motion, elemental motion and macro-motion.

2. The method of claim 1, further comprising refining identification of the activity, comprising analyzing timing of the identified activity.

3. The method of claim 2, wherein timing comprises at least one of an hour of a day, a day of a week, a week of a month, a month of a year.

4. The method of claim 1, further comprising refining identification of the activity, comprising analyzing at least one identified location of the identified activity.

5. The method of claim 1, further comprising refining identification of the activity, comprising analyzing a rate of change of a location of the animate or inanimate object.

6. The method of claim 1, further comprising refining identification of the activity, comprising analyzing patterns of a plurality of identified activities.

7. The method of claim 1, further comprising refining identification of the activity, comprising analyzing an age of the animate or inanimate object.

8. The method of claim 1, further comprising identifying a behavior of the animate or inanimate object.

9. The method of claim 8, wherein identifying a behavior of the animate or inanimate object comprises:
    identifying each activity of a sequence of activities of the animate or inanimate object; and
    identifying the behavior of the animate or inanimate object, comprising matching the sequence of identified activities of the animate or inanimate object with a stored sequences of activities, wherein each stored sequence of activities corresponds with an identified behavior.

10. The method of claim 9, further comprising tracking at least one behavior of the animate or inanimate object over time.

11. The method of claim 10, further comprising identifying patterns of the at least one behavior.

12. The method of claim 11, further comprising grouping the patterns of the animate or inanimate objects based on a common parameter between the animate or inanimate objects.

13. The method of claim 10, further comprising identifying changes in at least one behavior of the animate or inanimate object.

14. The method of claim 10, further comprising sending an alert upon identification of predetermined set of behavior changes.

15. The method of claim 10, wherein the device is attached to at least one of a human being or an vehicle that the human being is within, and further comprising identifying unsafe driving behavior of the human being.

16. The method of claim 1, wherein the stored acceleration signatures of the common library are useable for matching acceleration signatures of motions of multiple humans, and the stored acceleration signatures of the specific library are useable for matching acceleration signatures of motions of a particular human.

17. A method of identifying an activity of an animate or inanimate object, comprising:
    identifying, by one or more processors, each elemental motion of a sequence of elemental motions of a device attached to the animate or inanimate object; and
    identifying, by the one or more processors, the activity of the animate or inanimate object, comprising matching the sequence of identified elemental motions of the device with a library of stored sequences of elemental motions, wherein each stored sequence of elemental motions corresponds with an activities;
    identifying, by one or more processors, a behavior of the animate or inanimate object comprising;
    identifying, by the one or more processors, each activity of a sequence of activities of the animate or inanimate object; and
    identifying, by the one or more processors, the behavior of the animate or inanimate object, comprising matching the sequence of identified activities of the animate or inanimate object with a stored sequences of activities, wherein each stored sequence of activities corresponds with an identified behavior; and further comprising
    tracking at least one behavior of the animate or inanimate object over time;
    identifying, by the one or more processors, changes in at least one behavior of the animate or inanimate object;
    reducing a number of stored acceleration signature matches by identifying a previous activity of the object, and performing a time domain analysis on the filtered acceleration signal to identify transient signatures or steady-state signatures of the filtered acceleration signal.

18. A method of identifying an activity of an animate or inanimate object, comprising:
    identifying, by one or more processors, each elemental motion of a sequence of elemental motions of a device attached to the animate or inanimate object; and identifying, by the one or more processors, the activity of the animate or inanimate object, comprising matching the sequence of identified elemental motions of the device with a library of stored sequences of elemental motions, wherein each stored sequence of elemental motions corresponds with an activity;

identifying, by the one or more processors, a behavior of the animate or inanimate object comprising;

identifying, by the one or more processors, each activity of a sequence of activities of the animate or inanimate object; and identifying, by the one or more processors, the behavior of the animate or inanimate object, comprising matching the sequence of identified activities of the animate or inanimate object with a stored sequences of activities, wherein each stored sequence of activities corresponds with an identified behavior; and further comprising;

the device determining what network connections are available to the device; the device distributing at least some of the acceleration signature matching processing if processing capability is available to the device though available network connections.

19. The method of claim 18, wherein the device distributes the acceleration signature matching processing if the processing capability is available to the device through available network connections, and distributing the acceleration signature matching processing saves the device processing power.

20. An apparatus for identifying an activity of an animate or inanimate object, comprising:

a controller operative to:

identify each elemental motion of a sequence of elemental motions of device attached to the animate or inanimate object; and identify the activity of the animate or inanimate object, comprising matching the sequence of identified elemental motions of the object with stored sequences of elemental motions, wherein each stored sequence of elemental motions corresponds with an activity;

wherein identifying each elemental motion comprises that controller operative to:

generate an acceleration signature based on sensed acceleration of the device;

match the acceleration signature with at least one of a plurality of stored acceleration signatures, wherein each stored acceleration signatures corresponds with a type of motion;

identify the type of motion of the device based on the matching of the acceleration signature with the stored acceleration signature;

wherein the type of motion comprises at least one of atomic motion, elemental motion and macro-motion.

21. The apparatus of claim 20, wherein at least a portion of the controller is included within the device, and at least a portion of the controller is located external to the device.

22. The apparatus of claim 21, further comprising the controller operative to refine identification of the activity, comprising analyzing patterns of a plurality of identified activities.

23. The apparatus of claim 21, further comprising the controller operative to identify a behavior of the animate or inanimate object.

24. The apparatus of claim 23, wherein identifying a behavior of the animate or inanimate object comprises:

the controller operative to identify each activity of a sequence of activities of the animate or inanimate object; and the controller operative to identify the behavior of the animate or inanimate object, comprising matching the sequence of identified activities of the animate or inanimate object with a stored sequences of activities, wherein each stored sequence of activities corresponds with an identified behavior.

25. The apparatus of claim 24, further comprising the controller operative to track at least one behavior of the animate or inanimate object over time.

26. The apparatus of claim 25, further comprising the controller operative to identify patterns of the at least one behavior.

27. The apparatus of claim 26, further comprising the controller operative to group the patterns of the animate or inanimate objects based on a common parameter between the animate or inanimate objects.

* * * * *